(12) United States Patent
Sato et al.

(10) Patent No.: US 6,798,504 B2
(45) Date of Patent: Sep. 28, 2004

(54) APPARATUS AND METHOD FOR INSPECTING SURFACE OF SEMICONDUCTOR WAFER OR THE LIKE

(75) Inventors: Tatsuya Sato, Saitama-ken (JP); Yuichiro Kato, Saitama-ken (JP); Kenji Mitomo, Gunma-ken (JP)

(73) Assignee: Hitachi High-Tech Electronics Engineering Co., Ltd. (JP)

( * ) Notice: Subject to any disclaimer, the term of this patent is extended or adjusted under 35 U.S.C. 154(b) by 284 days.

(21) Appl. No.: 09/961,513

(22) Filed: Sep. 24, 2001

(65) Prior Publication Data

US 2002/0036771 A1 Mar. 28, 2002

(30) Foreign Application Priority Data

Sep. 26, 2000 (JP) ........................................ 2000-292676

(51) Int. Cl.[7] .............................................. G01N 21/88
(52) U.S. Cl. ...................................... 356/237.2; 356/30
(58) Field of Search ........................... 356/237.2, 237.3, 356/446, 30, 31

(56) References Cited

U.S. PATENT DOCUMENTS 4,449,818 A * 5/1984 Yamaguchi et al. ..... 356/237.3
4,794,264 A * 12/1988 Quackenbos et al. .... 356/237.2
6,118,525 A * 9/2000 Fossey et al. ............ 356/237.2
6,201,601 B1 * 3/2001 Vaez-Iravani et al. ... 356/237.4

* cited by examiner

Primary Examiner—Richard A. Rosenberger
(74) Attorney, Agent, or Firm—Rossi & Associates

(57) ABSTRACT

Light beam is irradiated onto a surface of a substrate to be inspected and scattered lights from the surface of the substrate are received at different light reception angles, so that first and second light detection signals corresponding to the different light reception angles are generated. Reference function defining a correlation in level value between the first and second light detection signals is set, a comparison is made between respective level values of the first and second light detection signals using the reference function as a comparison reference, and it is determined, on the basis of a result of the comparison, which of a plurality of different types of defects, such as a foreign substance and crystal-originated pit, a possible defect present on the surface of the substrate, which is represented by the light detection signals, corresponds to. Also, the level value of a predetermined one of a plurality of the light detection signals is weighted with a predetermined coefficient, and a comparison is made between the weighted level value of the predetermined light detection signal and the level value of the remaining light detection signal, to thereby identify any of a plurality of different types of defects, such as a foreign substance and scratch, present on the surface of the substrate.

13 Claims, 5 Drawing Sheets

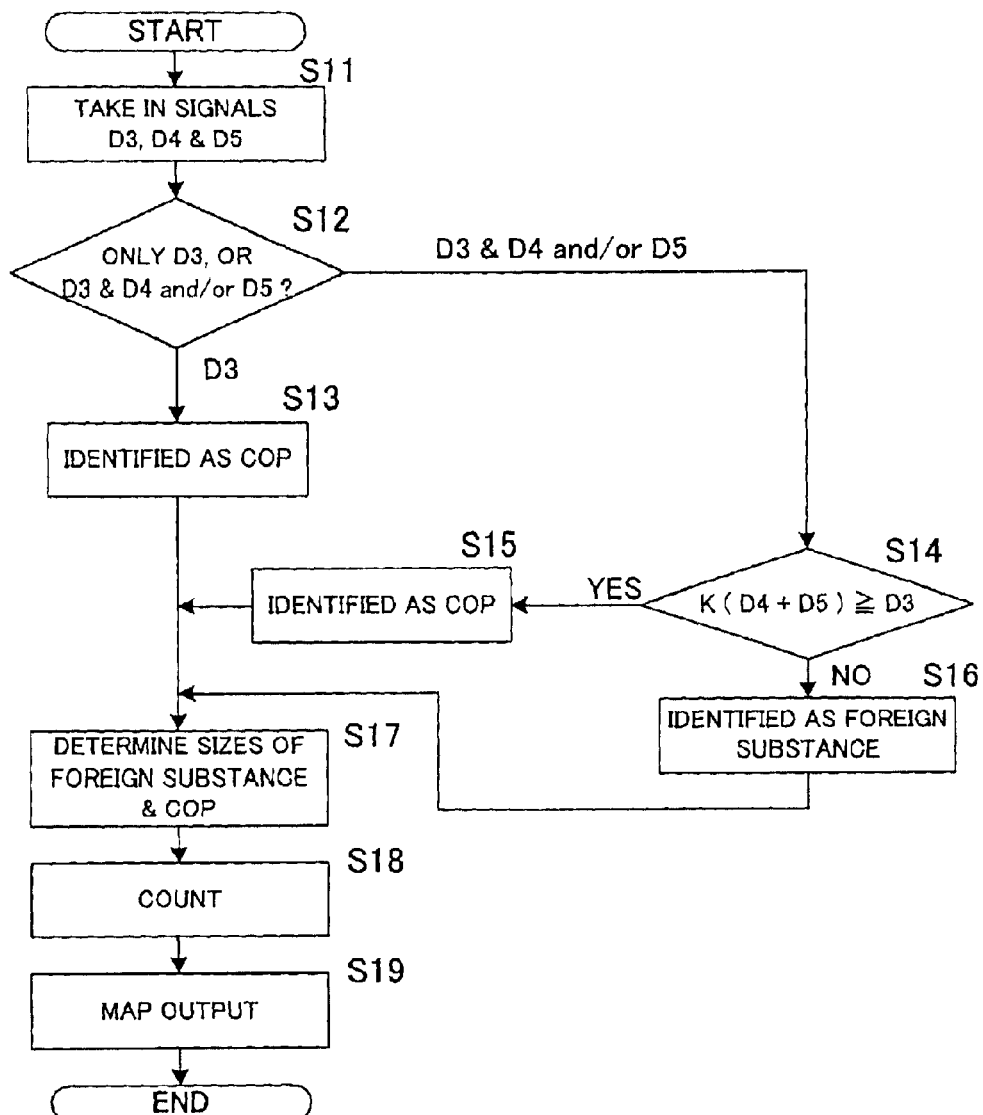
F I G. 8

APPARATUS AND METHOD FOR INSPECTING SURFACE OF SEMICONDUCTOR WAFER OR THE LIKE

BACKGROUND OF THE INVENTION

The present invention relates to surface inspection apparatus and methods for optically detecting defects present on a surface of a semiconductor substrate or the like and identifying respective types of the detected defects, and more particularly to an improved surface inspection apparatus and method which can distinguish, with an increased accuracy, between different types of defects present on a surface of a semiconductor wafer or the like, e.g., between foreign substances and crystal-originated pits or between foreign substances and scratches.

Generally, semiconductor wafers are made of high-purity polycrystalline silicon. Because the quality of the semiconductor wafer is greatly influenced by defects on the wafer surface, it has been conventional to carefully inspect the wafer surface using a surface inspection apparatus. Examples of the defects produced on the wafer surface include minute foreign substances such as dusts or polishing material or slurry adhered to the wafer surface, crystal-originated defects such as crystal-originated particles and pits, and scratches caused by surface polishing operations (polishing scratches). The crystal-originated pits (also known as "COPs") are produced in the wafer surface by minute oxidized silicon particles, formed on the wafer surface as a result of silicon atom oxidization, being caused to peel off the wafer surface due to the wafer surface polishing. The polishing scratches are formed as minute lines on the wafer surface.

To detect such various defects on and in the wafer surface, some of the conventional surface inspection apparatus use an optical defect detection method, in accordance with which a laser light beam is projected or irradiated onto the wafer surface and surface defects are detected by receiving reflected and scattered lights, from the wafer surface, of the laser light beam to examine optical characteristics of the received reflected and scattered lights that depend on shapes, sizes, etc. of possible defects on the wafer surface.

One example of the conventionally-known surface inspection apparatus for detecting foreign substances and crystal-originated pits present on and in the wafer surface is disclosed in Japanese Patent Laid-open Publication No. HEI-9-304289. The disclosed surface inspection apparatus is arranged to determine there is a foreign substance on the wafer surface when scattered lights, from the wafer surface, of the laser light beam projected or irradiated onto the wafer surface have been received by both of a low-angle photodetector (i.e., light receiving element) and medium-angle photodetector and determine that there is a crystal-originated pit in the wafer surface when a scattered light of the laser light beam has been received by only the medium-angle photodetector.

There has also been known another type of the surface inspection apparatus for detecting foreign substances and crystal-originated pits present on and in the wafer surface, which is arranged to determine that there is a foreign substance on the wafer surface when scattered lights, from the surface, of the laser light beam irradiated onto the wafer surface have been received by both of a high-angle photodetector and medium-angle photodetector and determine that there is a scratch on the wafer surface when a scattered light of the laser light beam has been received by only a low-angle photodetector.

Crystal-originated pits of various sizes and shapes tend to be produced in the wafer surface, because the depths and diameters of the pits differ depending on the extent with which the individual oxidized silicon particles peeled off the wafer surface. Therefore, with some crystal-originated pit having a particular shape, the lights, which should normally be scattered toward the medium-angle photodetector with predetermined directivity, may also be scattered with directivity in another direction. In such a case, not only the medium-angle photodetector but also the low-angle photodetector in the above-mentioned conventional surface inspection apparatus would undesirably detect the scattered lights caused by the crystal-originated pit, so that the crystal-originated pit would be erroneously detected as a foreign substance.

Also, scratches of various sizes and shapes tend to be produced on the wafer surface. Therefore, with some scratch having a particular shape, the lights, which should be scattered toward the low-angle photodetector with predetermined directivity, may also be scattered with directivity in another direction. In such a case, not only the low-angle photodetector but also the medium and high-angle photodetectors in the second-mentioned conventional surface inspection apparatus would detect the scattered lights caused by the scratch, so that the scratch would be erroneously detected as a foreign substance.

SUMMARY OF THE INVENTION

It is therefore an object of the present invention to provide a surface inspection apparatus and method which can distinguish, with a high accuracy, between a foreign substance and a crystal-originated pit on and in a substrate surface to be inspected.

It is another object of the present invention to provide a surface inspection apparatus and method which can distinguish, with a high accuracy, between a foreign substance and a scratch on a substrate surface to be inspected.

According to one aspect of the present invention, there is provided an improved surface inspection apparatus which comprises: an optical system that irradiates a light beam onto a surface of a substrate to be inspected and receives scattered lights from the surface of the substrate at different light reception angles, to thereby generate first and second light detection signals corresponding to the different light reception angles; and a processing device that sets a reference function defining correlations in level value between the first and second light detection signals, makes a comparison between respective level values of the first and second light detection signals using the reference function as a comparison reference, and determines, on the basis of a result of the comparison, which of a plurality of different types of defects a possible defect present on the surface of the substrate, represented by the light detection signals, corresponds to. With the inventive arrangements that the level values of the first and second light detection signals output from the optical scanning system are compared by use of the reference function defining the correlations in level between the first and second light detection signals and a determination is made, on the basis of the result of the comparison, as to which of the plurality of different types of defects a detected possible defect present on the surface of the substrate (e.g., semiconductor wafer) corresponds to, the present invention achieves a high-accuracy distinction between any foreign substances and crystal-originated pits present on and in the substrate surface.

According to another aspect of the present invention, there is provided a surface inspection apparatus which comprises: an optical system that irradiates a light beam onto a surface of a substrate to be inspected and receives scattered lights from the surface of the substrate at different light reception angles, to thereby generate a plurality of light detection signals corresponding to the different light reception angles; and a processing device that weights a level value of a predetermined one of the light detection signals with a predetermined coefficient, makes a comparison between the weighted level value of the predetermined light detection signal and a level value of the remaining light detection signal, and identifies, on the basis of a result of the comparison, any of a plurality of different types of defects present on the surface of the substrate. In the present invention, the level value of the predetermined light detection signal from among the plurality of light detection signals is weighted with the predetermined value to thereby differentiate the thus-weighted level of the light detection signal from the level of the remaining light detection signal (i.e., exaggerate the level difference between the predetermined light detection signal and the remaining light detection signal), so that identification operations optimal for each type of defect to be identified can be facilitated. Thus, by determining which one of the weighted level of the predetermined light detection signal and level of the remaining light detection signal is greater than the other, the present invention achieves a high-accuracy distinction between a foreign substance and a scratch present on the substrate surface.

The present invention may be constructed and implemented not only as the apparatus invention as discussed above but also as a method invention. Also, the present invention may be arranged and implemented as a software program for execution by a processor such as a computer or DSP, as well as a storage medium storing such a program. Further, the processor used in the present invention may comprise a dedicated processor with dedicated logic built in hardware, not to mention a computer or other general-purpose type processor capable of running a desired software program.

While the described embodiments represent the preferred form of the present invention, it is to be understood that various modifications will occur to those skilled in the art without departing from the spirit of the invention. The scope of the present invention is therefore to be determined solely by the appended claims.

BRIEF DESCRIPTION OF THE DRAWINGS

For better understanding of the object and other features of the present invention, its embodiments will be described in greater detail hereinbelow with reference to the accompanying drawings, in which:

FIG. 8 is a flow chart of a surface defect identification process, performed by the surface inspection apparatus of FIG. 6, for distinguishing between a foreign substance and a scratch on a wafer surface.

DETAILED DESCRIPTION OF THE INVENTION

Figure 1:
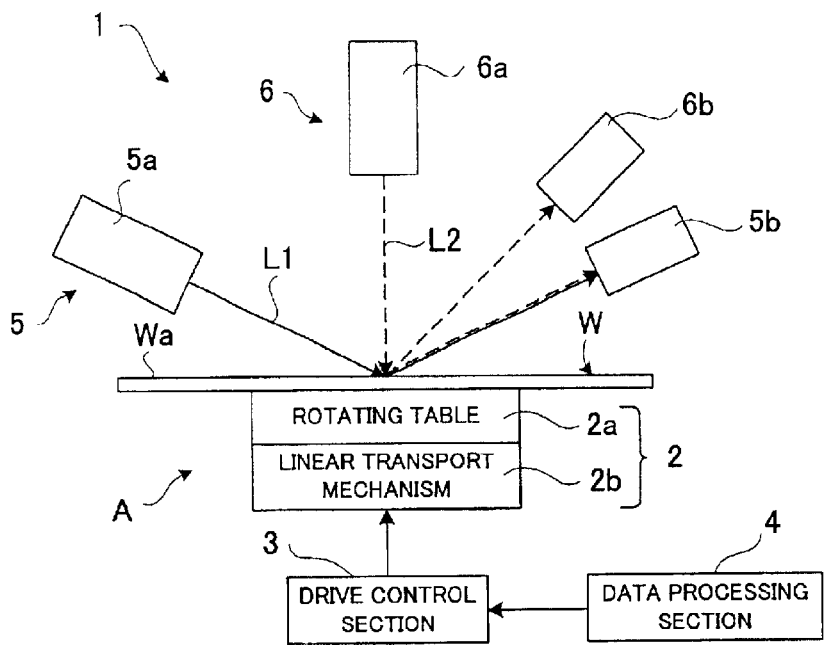
FIG. 1 is a block diagram showing a general setup of a surface inspection apparatus in accordance with a first embodiment of the present invention.

FIG. 1 is a block diagram showing a general setup of a surface inspection apparatus in accordance with a first embodiment of the present invention, which is arranged to detect and distinguish between foreign substances and crystal-originated pits present on and in a surface of a semiconductor wafer Wa. In FIG. 1, the surface inspection apparatus A includes an optical scanning system 1, a rotational and translational transport table unit 2, a drive control section 3, and a data processing section 4. Semiconductor wafer (hereinafter referred to simply as a "wafer") W to be inspected by the surface inspection apparatus A, which is made of high-purity polycrystalline silicon, is placed on the rotational and translational transport table unit 2. The optical scanning system 1 includes an optical section 5 for oblique-irradiation/low-angle photodetection (hereinafter "oblique-irradiation/low-angle photodetection optical section" 5) and an optical section 6 for normal-irradiation/medium-angle photodetection (hereinafter "normal-irradiation/medium-angle photodetection optical section" 6) which are both positioned above the surface Wa of the wafer W. The oblique-irradiation/low-angle photodetection optical section 5 includes an obliquely-irradiating light source 5a and a low-angle photodetector (light receiving element) 5b. These obliquely-irradiating light source 5a and low-angle photodetector 5b are disposed in respective predetermined positions with predetermined elevation angles relative to the surface Wa of the wafer W such that they can detect any crystal-originated pits (COPs) produced in the surface Wa of the wafer W. The normal-irradiation/medium-angle photodetection optical section 6 includes a normally-irradiating light source 6a and a medium-angle photodetector 6b. These normally-irradiating light source 6a and medium-angle photodetector 6b are disposed in respective predetermined positions with predetermined elevation angles, higher than those of the obliquely-irradiating light source 5a and low-angle photodetector 5b, relative to the surface Wa of the wafer W such that they can detect any foreign substances adhered to the surface Wa of the wafer W and crystal-originated pits produced in the surface Wa of the wafer W. The oblique-irradiation/low-angle photodetection optical section 5 projects or irradiates a first laser light beam L1 obliquely (at an oblique angle of incidence) onto the wafer surface Wa by means of the obliquely-irradiating light source 5a so that a laser light spot is formed on the wafer surface Wa, and it scans across the wafer surface Wa in a spiral pattern (this scanning is called a "spiral scan"). The normal-irradiation/medium-angle photodetection optical section 6 irradiates a second laser light beam L2 normally (at a normal angle of incidence) onto the wafer surface Wa by means of the normally-irradiating light source 6a so that a laser light spot is formed on the wafer surface, and it scans across the wafer surface in a spiral pattern, i.e. performs a spiral scan across the wafer surface Wa. In the instant embodiment, the spiral scan is performed by rotating the wafer W by means of a rotating table 2a and simultaneously translationally transporting the wafer W along the radius of the wafer W by means of a linear transport mechanism 2b. Of course, the spiral scan may be performed by rotating the wafer W by means of the rotating table 2a and simultaneously moving both of the optical sections 5 and 6 relative to the wafer W along the radius of the wafer W. Note that the rotational and translational transport table unit 2 in the instant embodiment is controlled by the drive control section 3 on the basis of instructions given from the data processing section 4. Further, the surface-inspecting scans by the optical sections 5 and 6 may be performed either simultaneously or separately from each other. In the case where the surface-inspecting scans by the optical sections 5 and 6 are performed simultaneously, light detection (light reception) signals output from the optical sections 5 and 6 as to a same given position of the wafer surface Wa can be used in real time in a surface defect identification process. In the case where the surface inspecting scans by the optical sections 5 and 6 are performed separately from each other, on the other hand, respective scanned results (light detection signals) obtained by the optical sections 5 and 6 are stored in memory and then the light detection signals as to a same given position of the wafer surface Wa are used in the surface defect identification process.

Figure 2:
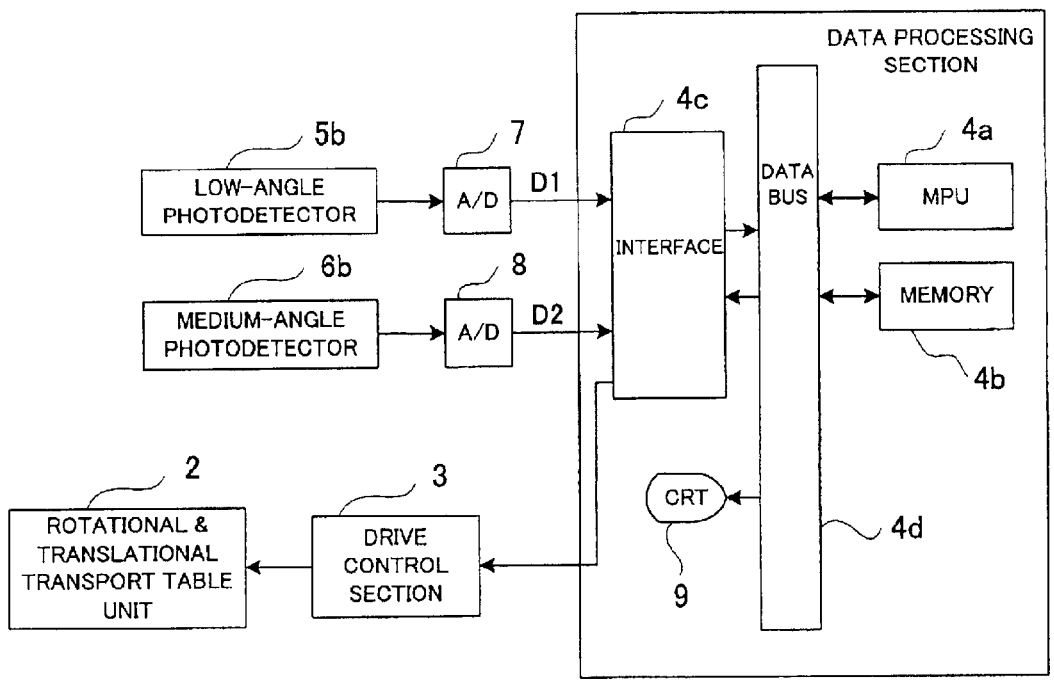
FIG. 2 is a block diagram showing a detailed organization of a data processing section in the surface inspection apparatus of FIG. 1.

If there are some defects, such as foreign substances and crystal-originated pits, on and in the flat surface Wa of the wafer W undergoing the spiral scans, the laser light beam is diffusively reflected or scattered from the wafer surface Wa due to the unevenness by the surface defects. Namely, each of the foreign substances is a projecting (convex) surface defect produced by a dust or dirt or slurry adhered to the wafer surface Wa, and such a foreign substance present on the wafer surface Wa causes the laser beam to be scattered in random directions. On the other hand, each of the crystal-originated pits is a concave surface defect produced by a minute oxidized silicon particle (crystal-originated particle), formed on the wafer surface Wa, being caused to peel off the wafer surface Wa, and such a crystal-originated pit present in the wafer surface Wa causes the laser beam to be scattered for the wafer surface Wa with scattered lights in a particular direction increased in level as compared to the remaining scattered lights in the other directions. In other words, while the foreign substance present on the wafer surface Wa causes non-directional scattered lights in random directions, the crystal-originated pit causes highly directional scattered lights with sharp directivity corresponding to its concave shape. Therefore, when there is a foreign substance on a same given laser-scanned position of the wafer surface Wa, the low-angle photodetector 5b and medium-angle photodetector 6b both detect scattered lights caused by the projecting foreign substance, but when there is a crystal-originated pit in the given laser-scanned position of the wafer surface Wa, only the medium-angle photodetector 6b detects scattered lights caused by the concave crystal-originated pit. Each of the low-angle photodetector 5b and medium-angle photodetector 6b, having received or detected the scattered lights, outputs a light detection signal D1 or D2 to the data processing section 4 via a corresponding A/D (Analog-to-Digital) converter 7 or 8, as shown in FIG. 2.

Generally, the depths and diameters of the crystal-originated pits considerably differ depending the extent with which the individual oxidized silicon particles peeled off the wafer surface Wa, as noted early in the introductory part of this patent specification. Thus, relatively great crystal-originated pits, typically those having a small depth but a great diameter, have a near-flat concave surface shape, and the scattered lights from such a near-flat concave surface will have an increased directional range, so that the scattered lights from the surface may be detected not only by the medium-angle photodetector 6b but also by the low-angle photodetector 5b. In case the scattered lights caused by the crystal-originated pit are detected by both the oblique-irradiation/low-angle photodetection optical section 5 and the normal-irradiation/medium-angle photodetection optical section 6 like this, the crystal-originated pit can not be distinguished from the foreign substance. To avoid such an inconvenience, the data processing section 4 in the instant embodiment is arranged to perform an improved surface defect identification process for the distinguishing between foreign substances and crystal-originated pits using a defect identifying table where is set a reference function defining correlations between detected light levels (luminance levels) of the first and second light detection signals D1 and D2. Namely, the surface defect identification process compares the detected light levels (luminance levels) of the first and second light detection signals D1 and D2 using, as a comparison reference, the reference function of the defect identifying table, and determines, on the basis of the comparison result, whether the possible defect present on the wafer surface Wa is a foreign substance or a crystal-originated pit.

Figure 3:
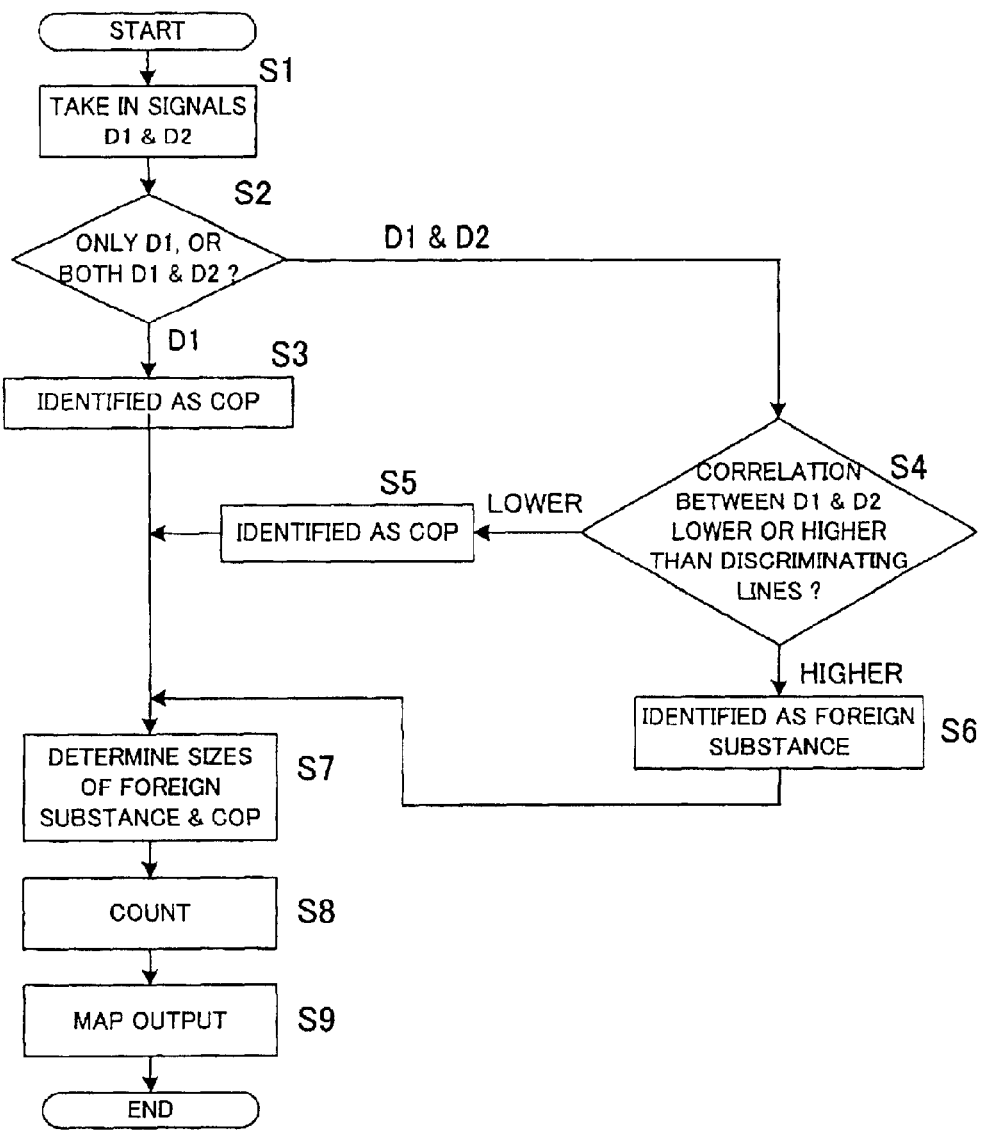
FIG. 3 is a flow chart of a surface defect identification process, performed by the surface inspection apparatus of FIG. 1, for distinguishing between a foreign substance and a crystal-originated pit on and in a wafer surface.

Now, a description will be made about the surface defect identification process performed by the data processing section 4, with reference to a flow chart of FIG. 3. At step S1, an MPU (Microprocessor Unit) 4a (FIG. 2) of the data processing section 4, which executes a program stored in a memory 4b (FIG. 2), takes in, for each scanned position on the wafer surface Wa, the first light detection signal D1 from the low-angle photodetector 5b and second light detection signal D2 from the medium-angle photodetector 6b via an interface 4c and data bus 4d of FIG. 2. At next step S2, a determination is made, for each scanned position on the wafer surface Wa, as to whether only the taken-in first light detection signal D1 from the low-angle photodetector 5b is greater a predetermined level for defect detection or both of the taken-in first and second light detection signals D1 and D2 are greater the predetermined level of for defect detection. If only the first light detection signal D1 has been found to be greater the predetermined level for defect detection as determined at step S2, i.e. if only the first light detection signal D1 represents an effective surface defect detection, then it is determined at step S3 that there is a crystal-originated pit at that scanned position on the wafer surface Wa (i.e. that the possible surface defect detected at the scanned position is identified as a crystal-originated pit), so that the MPU 4a proceeds to step S7. If, on the other hand, both of the taken-in first and second light detection signals D1 and D2 are greater the predetermined level for defect detection, the MPU 4a branches to step S4 in order to carry out surface defect distinction operations for distinguishing between a foreign substance and a crystal-originated pit. Where the surface inspection apparatus A is based on the scattered light measurement scheme, the second light detection signal D2 from the normal-irradiation/medium-angle photodetection optical section 6, which is representative of either a foreign substance or a crystal-originated pit, presents a given detected light level value. The first light detection signal D1 from the oblique-irradiation/low-angle photodetection optical section 5 presents a greater detected light level value when it is representative of (or corresponds to) presence of a foreign substance than when it is representative of (or corresponds to) presence of a crystal-originated pit. Correlations in the detected light level values of the first light detection signals D1 corresponding to foreign substances or crystal-originated pits present a similar tendency irrespective of the detected light level values represented by the second light detection signal D2 from the normal-irradiation/medium-angle photodetection optical section 6. Therefore, when the first and second light detection signals are both of a detected light level value representative of presence of a foreign substance or crystal-originated pit, it is possible to distinguish between the foreign substance and the crystal-originated pit in accordance with the magnitude of the detected light level of the first light detection signal D1 output from the oblique-irradiation/low-angle photodetection optical section 5 on the basis of the above-explained tendency. The MPU 4a distinguishes between the foreign substance and the crystal-originated pit, using a defect identifying table T (see FIG. 4) where is set a reference function on the basis of correlations between the detected light levels, representative of presence of foreign substances and crystal-originated pits, of the oblique-irradiation/low-angle photodetection optical section 5.

Figure 4:
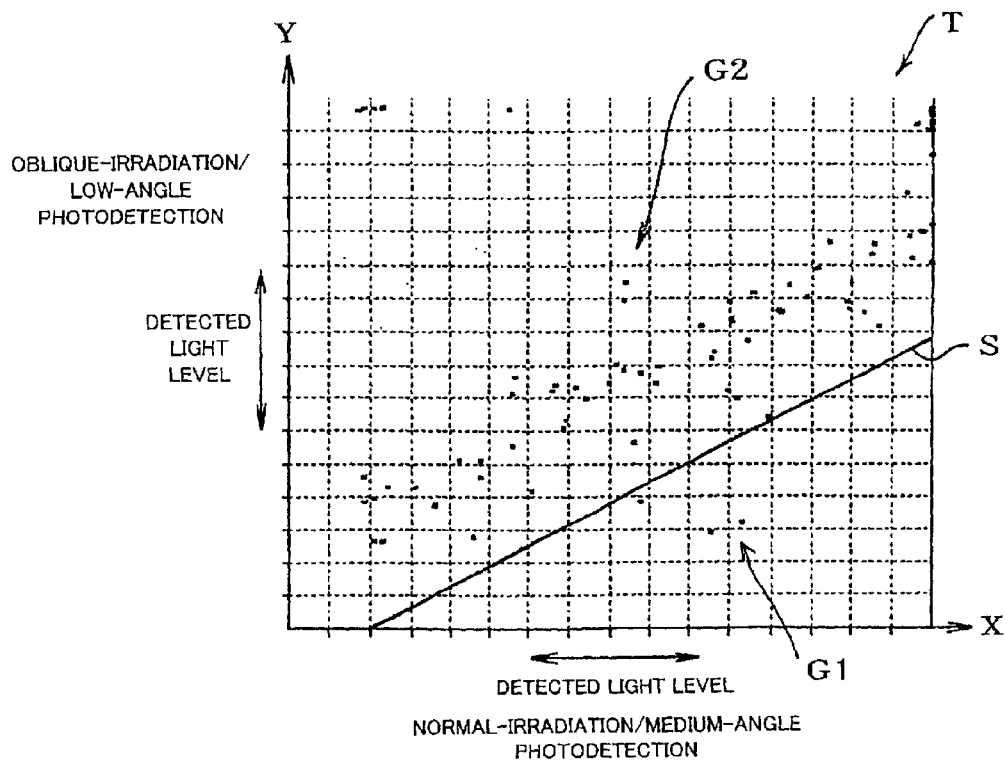
FIG. 4 is a diagram showing a distribution of luminance level data, representative of a foreign substance and crystal-originated pit, output from a normal-irradiation/medium-angle photodetection optical section and oblique-irradiation/low-angle photodetection optical section in the surface inspection apparatus.

As illustratively shown in FIG. 4, the horizontal axis (X axis) of the defect identifying table T represents the detected light level of the second light detection signal D2 from the normal-irradiation/medium-angle photodetection optical section 6, while the vertical axis (Y axis) of the defect identifying table T represents the detected light level of the first light detection signal D1 from the oblique-irradiation/low-angle photodetection optical section 5. In the illustrated example, a discriminating line S representing a primary function is set as the reference function. For example, the discriminating line S can be expressed by $$y=ax+b$$

where "a" represents an inclination based on a detected light level ratio between the normal-irradiation/medium-angle photodetection optical section 6 and the oblique-irradiation/low-angle photodetection optical section 5 determined for each of a plurality of kinds of reference particles having known particle diameters. "b" is an offset value of the detected light level of the oblique-irradiation/low-angle photodetection optical section 5. In a situation where the correlations in (i.e., combinations of) detected light level between the first and second light detection signals D1 and D2 present a distribution pattern as shown in black dots in FIG. 4, the MPU 4a determines a first group G1 of combinations of the detected light level data plotted in a region lower than the discriminating line S as representing a crystal-originated pit, at step S5 of FIG. 3. The MPU 4a also determines a second group G2 of combinations of the detected light level data plotted in a region higher than the discriminating line S as representing a foreign substance, at step S6. Then, the MPU 4a adds the first group G1 of the detected light level data, determined as representing crystal-originated pits, to the detection result of the crystal-originated pit determined at step S3. In this way, it is possible to distinguish between the foreign substances and the crystal-originated pits on the basis of the combinations of the first and second light detection signals D1 and D2. Then, at step S7, an operation is performed for determining respective sizes of the crystal-originated pit and foreign substance. At next step S8, an operation is performed for counting the so-far-identified crystal-originated pits and foreign substances to determine their respective running totals, at step S8. Then, a map output operation is performed, at step S9, for causing a CRT 9 of FIG. 2 to display a map indicative of respective positions, on the wafer surface Wa, the individual identified crystal-originated pits and foreign substances. Further, if the discriminating line S is expressed by an ordinary function, Y=f(X); thus, the crystal-originated pit and foreign substance can be distinguished from each other by determining whether the value of the first light detection signal D1 is greater or smaller than the value of "Y" obtained by substituting the level value of the signal D2 for X.

Figure 5:
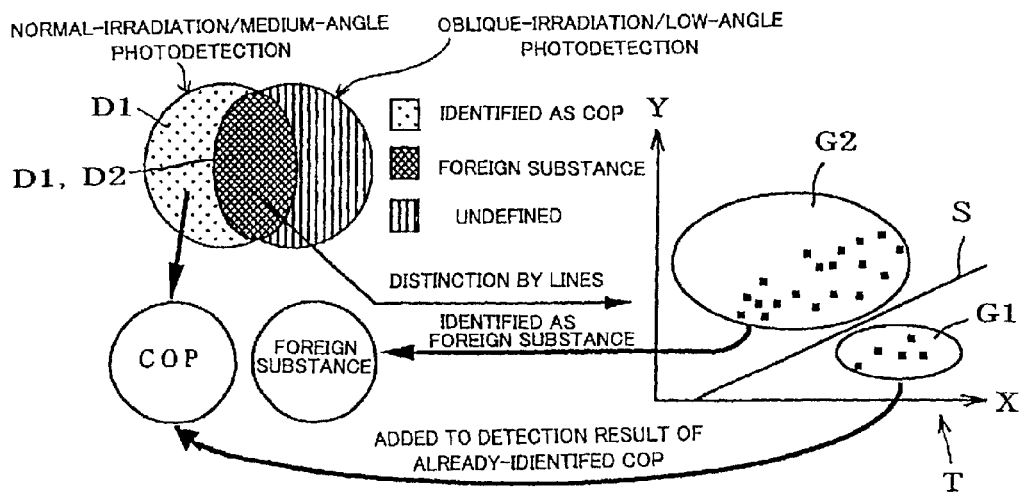
FIG. 5 is a diagram explanatory of operations for detecting and distinguishing between a foreign substance and a crystal-originated pit which is performed by a data processing section in the surface inspection apparatus.

FIG. 5 is a schematic diagram explanatory of the surface defect identification process performed by the MPU 4a of the data processing section 4 for distinguishing between the foreign substance and the crystal-originated pit. When only the normal-irradiation/medium-angle photodetection optical section 6 has output a light detection signal greater than the predetermined level value, the detected possible defect is identified as a crystal-originated pit. On the other hand, when both the normal-irradiation/medium-angle photodetection optical section 6 and the oblique-irradiation/low-angle photodetection optical section 5 have output light detection signals greater than the predetermined level value, a determination is made whether the detected possible defect is a foreign substance or a crystal-originated pit, on the basis of the above-mentioned discriminating line S of the defect identifying table T. Note that when only the oblique-irradiation/low-angle photodetection optical section 5 has output a light detection signal greater than the predetermined level value, this light detection signal is canceled as undefined. In the situation where individual combinations of detected light level data represented by the first and second light detection signals D1 and D2 present a distribution pattern as shown in black dots in the defect identifying table T of FIG. 4, the MPU 4a determines the first group G1 of the combinations of the detected light level data plotted in the region lower than the discriminating line S as representing a crystal-originated pit, and determines the second group G2 of the combinations of the detected light level data plotted in the region higher than the discriminating line S as representing a foreign substance. Namely, the foreign substance and crystal-originated pit can be distinguished from each other by determining whether the correlations or combinations of the detected light level data, represented by the first and second light detection signals D1 and D2 from the oblique-irradiation/low-angle photodetection optical section 5 and normal-irradiation/medium-angle photodetection optical section 6, fall in the region lower than the discriminating line S or in the region higher than the discriminating line S. The thus-identified crystal-originated pit is added to the detection result of the previously-identified crystal-originated pit or pits.

The instant embodiment has been described as setting the primary-functional discriminating line S in the defect identifying table T defining the correlations between the first and second light detection signals D1 and D2. However, the discriminating line S should not be construed as limited to the above-described; for example, the inclination "a" and offset value "b" may be set to any suitable values in accordance with the natures of defects to be identified. Further, the discriminating line S may be other than a primary function, such as a function including a curved line.

Figure 6:
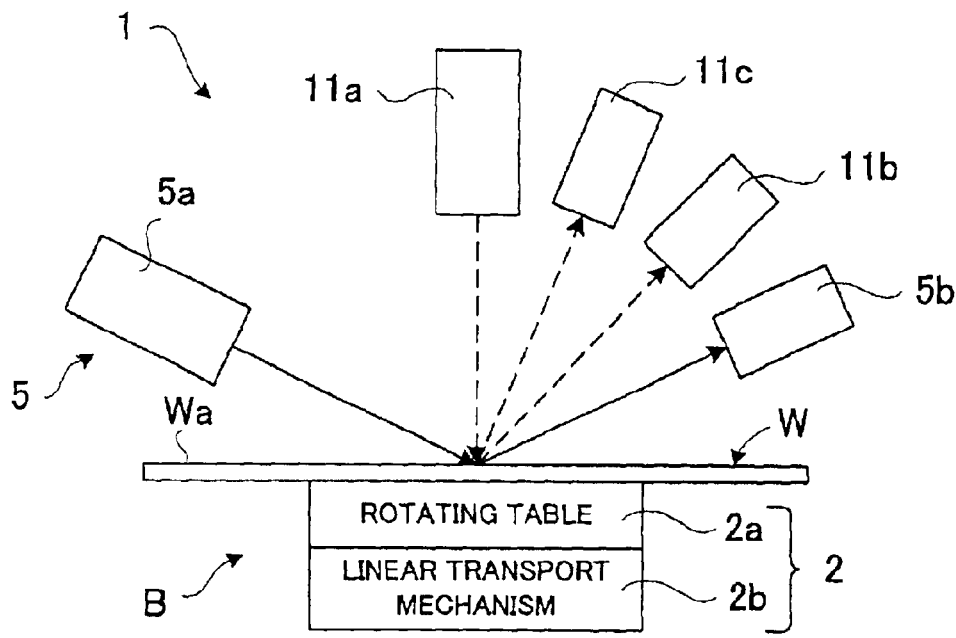
FIG. 6 is a block diagram showing a general setup of a surface inspection apparatus in accordance with a second embodiment of the present invention.

Next, a description will be made about a surface inspection apparatus B in accordance with a second embodiment of the present invention, with reference to FIG. 6 where same elements as in the above-described first embodiment of the surface inspection apparatus A are denoted by the same reference characters. This surface inspection apparatus B is arranged to detect and distinguish foreign substances and scratches present on the wafer surface Wa, and the optical scanning system 1 includes an optical section 5 for oblique-irradiation/low-angle photodetection (hereinafter "oblique-irradiation/low-angle photodetection optical section" 5) and an optical section 11 for normal-irradiation/medium- and high-angle photodetection (hereinafter "normal-irradiation/medium- and high-angle photodetection optical section" 11) both positioned above the wafer surface Wa. The oblique-irradiation/low-angle photodetection optical section 5 includes an obliquely-irradiating light source 5a and a low-angle photodetector (light receiving element) 5b. These obliquely-irradiating light source 5a and low-angle photodetector 5b are disposed in respective predetermined positions with predetermined elevation angles relative to the wafer surface Wa such that they can detect any scratches produced on the surface Wa of the wafer W. The normal-irradiation/medium- and high-angle photodetection optical section 11 includes a normally-irradiating light source 11a, a medium-angle photodetector 11b, and a high-angle photodetector 11c. These normally-irradiating light source 11a and photodetector 11b and 11c are disposed in respective predetermined positions with predetermined elevation angles, higher than those of the obliquely-irradiating light source 5a and low-angle photodetector 5b, relative to the surface Wa of the wafer W such that they can detect any foreign substances present on the surface Wa of the wafer W. As in the above-described first embodiment, the oblique-irradiation/low-angle photodetection optical section 5 projects or irradiates a first laser light beam L1 obliquely (at an oblique angle of incidence) onto the wafer surface Wa by means of the obliquely-irradiating light source 5a so that a laser light spot is formed on the wafer surface Wa, and performs a spiral scan across the wafer surface Wa. The normal-irradiation/medium- and high-angle photodetection optical section 11 irradiates a second laser light beam L2 normally (at a normal angle of incidence) onto the wafer surface Wa by means of the normally-irradiating light source 11a so that a laser light spot is formed on the wafer surface Wa, and performs a spiral scan across the wafer surface Wa. In the instant embodiment, the spiral scan is performed by rotating the wafer W by means of a rotating table 2a and simultaneously translationally transporting the wafer W along the radius thereof by means of a linear transport mechanism 2b. Of course, the spiral scan may be performed by rotating the wafer W by means of the rotating table 2a and simultaneously moving both of the optical sections 5 and 11 relative to the wafer W along the radius of the wafer W. Note that the surface-inspecting scans by the optical sections 5 and 11 may be performed either concurrently or separately from each other.

Figure 7:
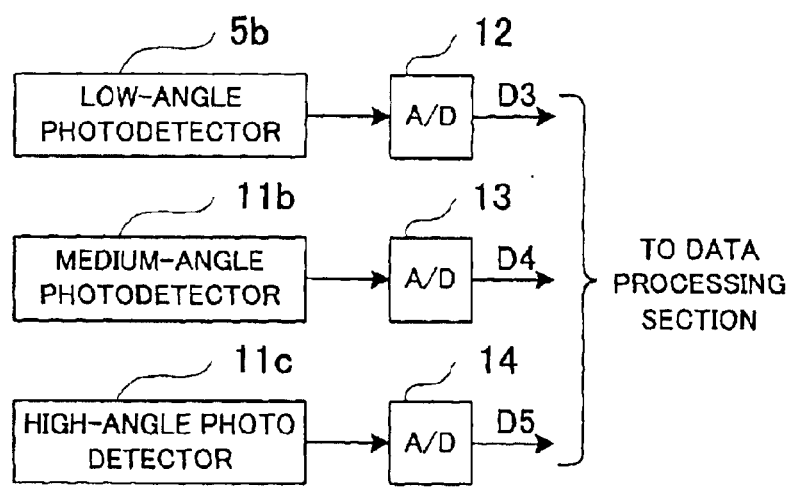
FIG. 7 is a block diagram showing a detailed organization of a data processing section in the surface inspection apparatus of FIG. 6.

If there are defects, such as foreign substances and scratches, on the flat surface Wa of the wafer W undergoing the spiral scans, the laser light beam is diffusively reflected or scattered from the wafer surface Wa due to the unevenness by the surface defects. Namely, because each of the foreign substances is a projecting (convex) surface defect produced by a dust or dirt or slurry adhered to the wafer surface Wa, such a foreign substance present on the wafer surface Wa causes the laser beam to be scattered in random directions. On the other hand, each of the scratches is a linear mark cut on the wafer surface Wa that is produced by polishing the wafer surface Wa, and thus such a scratch causes the laser beam to be scattered with lights scattered in a particular direction increased in level as compared to scattered lights in the other directions. In other words, while the foreign substance present on the wafer surface Wa causes non-directional scattered lights in random directions, the scratch on the wafer surface Wa causes directional scattered lights with sharp directivity corresponding to its depth and width. Therefore, when there is a foreign substance on a same given laser-scanned position of the wafer surface Wa, the medium-angle photodetector 11b and high-angle photodetector 11c both detect scattered lights caused by the projecting foreign substance, but when there is a scratch on the given laser-scanned position of the wafer surface Wa, only the low-angle photodetector 5b detects scattered lights caused by the scratch. Each of the low-angle photodetector 5b, medium-angle photodetector 11b and high-angle photodetector 11c, having received or detected the scattered lights, outputs a light detection signal D3, D4 or D5 to a data processing section 4 via a corresponding A/D converter 12, 13 or 14, as shown in FIG. 7. Although not specifically shown in FIG. 7, the data processing section 4 in the second embodiment includes an interface, data bus, MPU, memory and CRT similar to those in the first embodiment of FIG. 2.

Because the depths and diameters of the scratches differ considerably depending the sizes of the linear marks cut on the wafer surface Wa by the wafer surface polishing, relatively great scratches, typically those having a small depth but a great width, has a near-flat concave surface shape, and the scattered lights from such a near-flat concave surface will have an increased directional range, so that the scattered lights from the surface may be detected not only by the low-angle photodetector 5b but also by the medium-angle photodetector 11b and high-angle photodetector 11c. Particularly, the high-angle photodetector 11c would undesirably detect scattered lights caused by a relatively great scratch. Note that the medium-angle photodetector 11b is provided for scattered lights that can not be by the high-angle photodetector 11c, i.e. for supplementing the light detecting function of the high-angle photodetector 11c. Heretofore, when scattered lights caused by scratches were detected not only by the oblique-irradiation/low-angle photodetection optical section but also by the normal-irradiation/medium- and high-angle photodetection optical section, these scratches were all identified as foreign substances; as compared to this, the second embodiment of the present invention is arranged to appropriately distinguish between foreign substances and scratches. Namely, in the second embodiment, the data processing section 4 weights the detected light level data (luminance level data), represented by the light detection signals D4 and D5, with a predetermined value K that is a decimal value smaller than "1", and compares the thus-weighted detected light level data and the detected light level data represented by the light detection signal D3 to thereby distinguish between the foreign substance and the scratch, as will be later described in detail.

Now, a description will be made about a surface defect identification process performed by the data processing section 4 in the second embodiment, with reference to a flow chart of FIG. 8. At step S11, the MPU (Microprocessor Unit) 4a of the data processing section 4, which executes a program stored in the memory 4b, takes in, for each scanned position on the wafer surface Wa, the light detection signal D3 from the low-angle photodetector 5b and light detection signals D4 and D5 from the medium-angle photodetector 6b and high-angle photodetector 6c via the interface 4c and data bus 4d. At next step S12, a determination is made, for each scanned position on the wafer surface Wa, as to whether only the taken-in light detection signal D3 from the low-angle photodetector 5b is greater a predetermined level for defect detection or the taken-in light detection signals D3, D4 and/or D5 from the low-angle photodetector 5b, medium-angle photodetector 6b and high-angle photodetector 6c are each greater the predetermined level for defect detection. If only the taken-in light detection signal D3 has been found to be greater the predetermined level for defect detection as determined at step S12, i.e. if only the light detection signal D3 represents an effective surface defect detection, then it is determined at step S13 that there is a scratch at the scanned position of the wafer surface Wa (i.e., that the possible surface defect detected at the scanned position is identified as a scratch), and so that the MPU 4a proceeds to step S17. If, on the other hand, the taken-in light detection signals D3, D4 and/or D5 are each greater the predetermined level for defect detection as determined at step S12, the MPU 4a branches to step S14 in order to carry out surface defect distinction operations for distinguishing between a foreign substance and a scratch.

Namely, at step S14, a comparison is made between a value, obtained by multiplying a sum of detection level data values represented by the light detection signals D4 and D5 by the predetermined coefficient K (i.e., K(D4+D5)), and a detected light level data value represented by the remaining light detection signal D3. By thus weighting the detected light level data represented by the light detection signals D4 and D5, output from the normal-irradiation/medium- and high-angle photodetection optical section 11, with the predetermined coefficient K, it is possible to clearly differentiate (exaggerate a level difference between) the light detection signals D4 and D5 weighted with the coefficient K and the light detection signal D3 obtained from the oblique-irradiation/low-angle photodetection optical section 5. If K(D4+D5)≧D3 (i.e., YES determination at step S14), it is determined at step S15 that there is a scratch at the scanned position of the wafer surface Wa (i.e., that the possible surface defect detected at the scanned position is identified as a scratch), while if K(D4+D5)<D3 (i.e., NO determination at step S14), it is determined at step S16 that there is a foreign substance at the scanned position of the wafer surface Wa (i.e., that the possible surface defect detected at the scanned position is identified as a foreign substance). In other words, if the product between the sum of the values of the light detection signals D4 and D5 from the normal-irradiation/medium- and high-angle photodetection optical section 11 and the coefficient K (decimal value less than "1") is greater than the value of the light detection signal D3 from the oblique-irradiation/low-angle photodetection optical section 5, the detected possible defect is identified as a scratch; otherwise, the detected possible defect is identified as a foreign substance. Stated otherwise, if the light detection signals D4 and D5 are considerably greater in level than the light detection signal D3, the detected possible defect is identified as a scratch. Then, the scratch identified at step S16 is added to the detection result of the scratch identified at step S13. Once the operations for distinguishing between the foreign substance and the scratch using the light detection signals D3, D4 and D5 have been completed, a size determination operation is performed at step S17 for determining the sizes of the identified scratch and foreign substance. After that a count operation is performed at step S18 for counting the so-far identified scratches and foreign substances to provide their respective running totals. After that, a map output operation is performed, at step S19, for causing the CRT 9 to display a map indicative of respective positions, on the wafer surface Wa, the individual identified crystal-originated pits and foreign substances.

With the arrangements that the detected light level data represented by the light detection signals D4 and D5, output from the normal-irradiation/medium- and high-angle photodetection optical section 11, are weighted with the predetermined value and then compared with the detected light level data represented by the light detection signal D3 output from the oblique-irradiation/low-angle photodetection optical section 5, the instant embodiment achieves a high-accuracy distinction between foreign substances and scratches. It should be appreciated that the normal-irradiation/medium- and high-angle photodetection optical section 11 in the optical scanning system 1 may be replaced with a normal-irradiation/high-angle photodetection optical section including only the normally-irradiating light source 11a and high-angle photodetector 11c. Further, the light detection signal D3, rather than the light detection signals D4 and D5, may be multiplied by the coefficient K, in which case the coefficient K is set to a value greater than "1" including a decimal fraction.

Note that whereas the embodiments of the present invention have been described in relation to the case where a laser light beam is used as the scanning light beam, the laser light beam may be replaced with a white light or ultraviolet light beam. Further, while the embodiments have been described as performing the spiral scan across the wafer surface to be inspected, the scan may be performed in a two-dimensional X-Y scan pattern. Further, while the embodiments have been described as applied to the surface inspection of semiconductor wafer substrates, the present invention may be applied to surface inspection of glass substrates and the like.

In summary, the present invention is characterized in that levels of first and second light detection signals output from the optical scanning system are compared by use of a reference function defining correlations in level between the first and second light detection signals and a determination is made, on the basis of a result of the comparison, as to which of a plurality of different types of surface a detected possible defect present on the surface of a substrate corresponds to. With such arrangements, the present invention achieves a high-accuracy distinction between a foreign substance and a crystal-originated pit present on and in the substrate surface.

The present invention is also characterized in that a level of a predetermined light detection signal is weighted with a predetermined value to thereby differentiate the thus-weighted level of the light detection signal from a level of the remaining light detection signal. Thus, by determining which one of the weighted level of the predetermined light detection signal and level of the remaining light detection signal is greater than the other, the present invention achieves a high-accuracy distinction between a foreign substance and a scratch present on the substrate surface.

What is claimed is:

1. A surface inspection apparatus comprising:
an optical system that irradiates a first and second light beams onto a same given position on a surface of a substrate to be inspected and receives scattered lights from the same given position on the surface of the substrate, but at different light reception angles, to thereby generate first and second light detection signals corresponding to the different light reception angles; and
a processing device that sets a reference function defining a correlation in level value between said first and second light detection signals, makes a comparison between respective level values of said first and second light detection signals using the reference function as a comparison reference, and determines, on the basis of a result of the comparison, which of a plurality of different types possible defects present on the surface of the substrate, represented by the light detection signals, corresponds to, wherein the reference function is a predetermined function expressed as Y=f(X), and wherein the type of the possible defect as identified depending in whether the predetermined function Y, where X represents the level value of one of said first and second light detection signals, is greater or smaller than the level value of the other of said first and second light detection signals.

2. A surface inspection apparatus as claimed in claim 1, wherein the substrate is a semiconductor wafer, and the plurality of different types of defects include at least a foreign substance and crystal-originated pit on and in a surface of the semiconductor wafer.

3. A surface inspection apparatus as claimed in claim 1, wherein said optical system includes:

a first optical section that irradiates the first light beam onto the given position on the surface of the substrate at a predetermined low angle of incidence relative to the surface of the substrate and receives a scattered light, from the surface of the substrate, of the light beam at a predetermined low light reception angle, to thereby generate the first light detection signal; and a second optical section that irradiates the second light beam onto the same given position on the surface of the substrate at a predetermined high angle of incidence, higher than the predetermined low angle of incidence of said first optical section, relative to the surface of the substrate and receives a scattered light, from the surface of the substrate, of the light beam at a predetermined high light reception angle higher than the predetermined low light reception angle of said first optical section, to thereby generate the second light detection signal.

4. A surface inspection apparatus comprising:

an optical system that irradiates first and second light beams onto a same given position on a surface of a substrate to be inspected and receives scattered lights from the same given position on the surface of the substrate, but at different light reception angles, to thereby generate first and second light detection signals corresponding to the different light reception angles; and a processing device that sets a reference function defining a correlation in level value between said first and second light detection signals, makes a comparison between respective level values of said first and second light detection signals using the reference function as a comparison reference, and determines, on the basis of a result of the comparison, which of a plurality of different types of possible defects present on the surface of the substrate, represented by the light detection signals, corresponds to, wherein said processing device includes a table storing combinations of the level values of said first and second light detection signals, the combinations of the level values being classified into at least two groups in accordance with the reference function, the at least two groups being associated with the plurality of different types of defects, and wherein said table is consulted in accordance with a particular one of the combinations of the level values of said first and second light detection signals pertaining to the same given position on the surface of the substrate, to determine which one of the groups in said table the particular combination of the level values of said first and second light detection signals belongs to, so as to identity a type of the possible defect in accordance with the one group the particular combination of the level values belongs to.

5. A surface inspection apparatus as claimed in claim 4, wherein said processing device performs a defect identification process for identifying the possible defect as a predetermined first type defect when the level value of said first light detection signal is not greater than a predetermined level value and only the level value of said second light detection signal is greater than the predetermined level value, and wherein when the level values of both of said first and second light detection signals are greater than the predetermined level value, said processing device determines whether the possible defect is the predetermined first type defect or a predetermined second type defect.

6. A surface inspection apparatus comprising:

an optical system that irradiates a plurality of light beams onto a same given position on a surface of a substrate to be inspected and receives scattered lights from the same given position on the surface of the substrate, but at different light reception angles, to thereby generate a plurality of light detection signals corresponding to the different light reception angles; and a processing device that weights a level value of a predetermined one of the light detection signals with a predetermined coefficient, makes a comparison between the weighted level value of the predetermined light detection signal and a level value of the remaining light detection signal, and identifies, on the basis of a result of the comparison, any of a plurality of different types of defects present on the surface of the substrate.

7. A surface inspection apparatus as claimed in claim 6, wherein said optical system includes:

a first optical section that irradiates a first light beam onto the given position on the surface of the substrate at a predetermined low angle of incidence relative to the surface of the substrate and receives a scattered light, from the surface of the substrate, of the first light beam at a predetermined low light reception angle, to thereby generate a first light detection signal; and a second optical section that irradiates a second light beam onto the same given position on the surface of the substrate at a predetermined high angle of incidence, higher than the predetermined low angle of incidence of said first optical section, relative to the surface of the substrate and receives a scattered light, from the surface of the substrate, of the second light beam at a predetermined high light reception angle higher than the predetermined low light reception angle of said first optical section, to thereby generate a second light detection signal, and wherein said processing device identifies a possible defect on the surface of the substrate, represented by the light detection signals, as a predetermined first type defect when only the level value of said first light detection signal is greater than a predetermined level value and the level value of said second light detection signal is not greater than the predetermined level value, and wherein when the level values of both of said first and second light detection signals are greater than the predetermined level value, said processing device weights the level value of a predetermined one of said first and second light detection signals with a predetermined coefficient, makes a comparison between the weighted level value of the predetermined light detection signal and the level value of the other light detection signal, and determines, on the basis of a result of the comparison, which one of the predetermined first and second type defects the possible defect corresponds to.

8. A surface inspection apparatus as claimed in claim 7, wherein said second optical section further generates a third light detection signal by receiving a scattered light, from the same given position on the surface of the substrate, of the second light beam at a predetermined light reception angle different from the light reception angle of said second light detection signal, and wherein when the level values of said first light detecting signal and said second and said third light detection signal are or said third light detection is greater than the predetermined level value, said processing device weights one of the level value of said first light detection signal and a summed level value of said second and third light detection signals with a predetermined coefficient, makes a comparison between the weighted level value and the level value of the remaining light detection signal, and determines, on the basis of a result of the comparison, which one of said predetermined first and second type defects the possible defect corresponds to.

9. A surface inspection apparatus as claimed in claim 6, wherein the substrate is a semiconductor wafer, and the plurality of different types of defects include at least a foreign substance and scratch on a surface of the semiconductor wafer.

10. A surface inspection method comprising the steps of:

irradiating first and second light beams onto a same given position on a surface of a substrate to be inspected and receiving scattered lights from the same given position on the surface of the substrate, but at different light reception angles, to thereby generate first and second light detection signals corresponding to the different light reception angles; and setting a reference function defining a correlation in level value between said first and second light detection signals, making a companion between respective level values of said first and second light detection signals using the reference function as a comparison reference, and determining, on the basis of a result of the comparison, which of a plurality of different types of possible defects on the surface of the substrate, represented by the light detection signals, corresponds to, wherein the reference function is a predetermined function expressed as Y=f(X), and wherein the type of the possible defect is identified depending on whether the predetermined function Y, where X represents the level value of one of said first and second light detection signals, is greater or smaller than the level value of the other of said first and second light detection signals.

11. A surface inspection method comprising the steps of:

irradiating first and second light beams onto a same given position on a surface of a substrate to be inspected and receiving scattered lights from the same given position on the surface of the substrate, but at different light reception angles, to thereby generate first and second light detection signals corresponding to the different light reception angles;

identifying the possible defect as a predetermined first type defect when the level value of said first light detection signal is not greater than a predetermined level value and only the level value of said second light detection signal is greater than the predetermined level value, and when the level values of both of said first and second light detection signals are greater than the predetermined level value, determining whether the possible defect is a predetermined first type defect or a predetermined second type defect depending on which one of at least two groups a combination of the level values of said first and second Light detection signals belongs to, wherein said at least two groups are defined by a table storing combinations of the level values of said first and second light detection signals, the combinations of the level values being classified into said at least two groups associated with the different types of defects.

12. A surface inspection method comprising the steps of:

irradiating a plurality of light beams onto a same given position on a surface of a substrate to be inspected and receiving scattered lights from the same given position on the surface of the substrate, but at different light reception angles, to thereby generate a plurality of light detection signals corresponding to the different light reception angles; and weighting a level value of a predetermined one of the light detection signals with a predetermined coefficient, making a comparison between the weighted level value of the predetermined light detection signal and a level value of the remaining light detection signal, and identifying, on the basis of a result of the comparison, any of a plurality of different types of defects present on the surface of the substrate.

13. A surface inspection method comprising the steps of:

irradiating first and second light beams onto a same given position on a surface of a substrate to be inspected and receiving scattered lights from the same given position on the surface of the substrate, but at different light reception angles, to thereby generate first and second light detection signals corresponding to the different light reception angles;

identifying a possible defect on the surface of the substrate, represented by the light detection signals, as a predetermined first type defect when only a level value of said first light detection signal is greater than a predetermined level value and a level value of said second light detection signal is not greater than the predetermined level value, and the level values of both of said first and second light detection signals are greater than the predetermined level value, weighting the level value of a predetermined one of said first and second light detection signals with a predetermined coefficient, making a comparison between the weighted level value of the predetermined light detection signal and the level value of the remaining light detection signal, and determining, on the basis of a result of the comparison, which one of predetermined first and second type defects the possible defect corresponds to.

* * * * *